United States Patent [19]

Nagasawa et al.

[11] Patent Number: 4,622,389

[45] Date of Patent: Nov. 11, 1986

[54] NOVEL SUBSTRATE FOR DETERMINING THE ACTIVITY OF BLOOD COAGULATION FACTOR XA (STUART-PROWER FACTOR)

[75] Inventors: Takeshi Nagasawa, Urawa; Yoshio Nakamura, Koriyama; Tsuyoshi Enomoto, Koriyama; Katsumasa Kuroiwa, Koriyama, all of Japan

[73] Assignee: Nitto Poseki Co., Ltd., Fukushima, Japan

[21] Appl. No.: 732,396

[22] Filed: May 9, 1985

[30] Foreign Application Priority Data

May 16, 1984 [JP] Japan ................... 59-98355

[51] Int. Cl.[4] .......................... C07K 5/08; C12Q 1/56
[52] U.S. Cl. ..................... 530/331; 530/802; 435/13
[58] Field of Search ................ 530/331, 802; 435/13

[56] References Cited

U.S. PATENT DOCUMENTS 4,452,736  6/1984  Nagasawa et al. ................ 530/331

Primary Examiner—Delbert R. Phillips
Attorney, Agent, or Firm—Bert J. Lewen; Henry Sternberg

[57] ABSTRACT

A novel chromogenic and fluorescent substrate for determining the activity of blood coagulation factor Xa and Xa-like enzymes. The novel substrate according to the present invention has very excellent selectivity as compared with the hitherto disclosed substrates and enables specific determination of blood coagulation factor Xa. The present substrate is therefore useful for the studies of chemical reactions involving formation, inhibition and consumption of factor Xa and can be also used for the determination of various factors associated therewith such as factor X, anti-Xa factor, factor VII, factor VIII, factor IX and heparin.

1 Claim, No Drawings

NOVEL SUBSTRATE FOR DETERMINING THE ACTIVITY OF BLOOD COAGULATION FACTOR XA (STUART-PROWER FACTOR)

FIELD OF THE INVENTION

The present invention relates to a novel chromogenic and fluorescent substrate for determining the activity of blood coagulation factor Xa and Xa-like enzymes. The novel substrate according to the present invention has very excellent selectivity as compared with the hitherto disclosed substrates and enables specific determination of blood coagulation factor Xa. The present substrate is therefore useful for the studies of chemical reactions involving formation, inhibition and consumption of factor Xa and can be also used for the determination of various factors associated therewith such as factor X, anti-Xa factor, factor VII, factor VIII, factor IX and heparin.

DESCRIPTION OF THE PRIOR ART

Introduction of synthetic substrates into the blood coagulation and fibrinolysis reactions was initiated by the use of arginine esters such as TAMe (Tos-Arg-OMe) synthesized by S. Shermy et al., [Journal of Biological Chemistry, 208, 85–105 (1954)] as a substrate for the determination of esterase activity of thrombin in 1954. Practical application of such synthetic substrates has initially involved some serious problems such as non-agreement of hydrolytic activity of esters with coagulation activity, and low specificity and sensitivity of the substrates. These problems, however, have been alleviated by many significant achievements in the art. From the progress of peptide chemistry in recent years, a peptide substrate Bz-Phe-Val-Arg-PNA (S-2160) resembling the amino-acid structure of the thrombin-cleaved portion of fibrinogen was synthesized by Blömbach et al., [Thrombosis Research, Vol. 1, pp. 267–278 (1972)], and the technology was developed for the simple enzymochemical spectroscopic analysis by yellow color development of p-nitroaniline (PNA) isolated by an enzymatic reaction. Preparation of reagents was also made easy, on the basis of these achievements, said synthetic substrates have come to be practically used for the studies and examinations of blood coagulation factors.

Factor Xa is a proteolytic enzyme which is formed by the activation of factor X, an enzyme precursor, in the blood coagulation cascade and is combined with phospholipide and calcium ions to proteolyze factor II (prothrombin) at two points of peptide chain to turn it into factor IIa (thrombin). Formation of factor X is reduced on contraction of specific diseases or ailments such as hepatic trouble, vitamin deficiencies, etc. Genetic trouble relating to the synthesis in formation of factor X also causes a corresponding decrease of formation of factor X. It is therefore of much account that the determination of factor Xa in blood plasma can be made by a simple and accurate method.

On the other hand, for the synthetic substrate to be used for the determination of enzymatic activity, it is important to meet the following four requirements: (1) high sensitivity and (2) high specificity to the enzyme to be determined, (3) good solubility in water and biological test liquids, and (4) easy detectability of liberated product.

Among of these, high specificity to the enzyme to be determined is especially important.

Generally, in the determination of factor X or anti-factor Xa in plasma by utilizing a chromogenic substrate, there can hardly be obtained an accurate result of determination when a cross reaction takes place between said substrate and blood coagulation-fibrinolysis factors other than factor Xa which is expected to exist in plasma, for example plasmin, thrombin, urokinase and the like.

Tetrapeptide derivatives are disclosed in DT-OS 2,552,570 as the best substrate for factor Xa ever developed. Bz-Ile-Glu-Gly-Arg-PNA (S-2222) is cited as an example of tetrapeptide derivatives which are hydrolyzed by factor Xa to form p-nitroaniline. Such tetrapeptide derivatives, however, are not always satisfactory in respect of substrate specificity; it is known that such derivatives are reacted not only with factor Xa but also with other blood coagulation-fibrinolysis factors such as plasmin, urokinase and thrombin.

Further, because of poor solubility in water-soluble media, said tetrapeptide derivatives can not be used for a factor Xa analysis which is to be conducted in a saturated state of substrate. For instance, in case the concentration of factor Xa to be determined in morbid plasma is low, said tetrapeptide derivatives are not enough sensitive as to allow obtainment of a corresponding accurate determination. Also, if the amount of factor Xa is increased by further addition of plasma, there takes place sedimentation of tetrapeptide substrate under the influence of plasma protein, making it unable to conduct the enzyme activity analysis.

Also, the colorimetic method in which yellow color of produced p-nitroaniline is compared as in the case of said substrate is subject to the influence of plasma components.

In order to eliminate such difficulties in the prior art, the present inventors have made further studies for the development of a novel substrate useful for determining the activity of blood coagulation factor Xa and, as a result, found out a substrate which is amazingly improved over said defects of the conventional substrates and has the excellent properties that can satisfy the afore-mentioned four requirements.

SUMMARY OF THE INVENTION

An object of the present invention is to provide novel substrate for determining the activity of blood coagulation factor Xa (Stuart-Prower factor).

Another object of the present invention is to provide a method for determining the activity of blood coagulation factor Xa.

DETAILED EXPLANATION OF THE INVENTION

The novel chromogenic fluorescent substrate according to the present invention is represented by the following general formula (I):

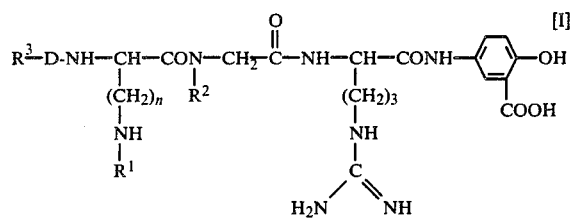

[wherein n is a number of 3 to 4; R¹ is —H or

R² is —H, —CH₃ or

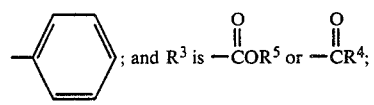
; and R³ is —COR⁵ or —CR⁴;

and in the above definitions, R⁴ is —H, —CH₃,

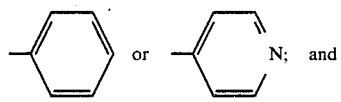

R⁵ is 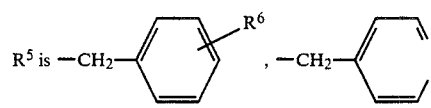

or —C(CH₃)₃ (R⁶=H or CH₃O)] and is characterized by the use of 3-carboxy-4-hydroxy-anilide (CHA) as chromogenic group. The present substrate has excellent solubility in water because of the possession of extremely hydrophilic groups, i.e., hydroxyl and carboyxl groups as chromogenic groups. In a typical example of practical use, the substrate of the general formula (I) is used as a substrate for the determination of blood coagulation factor Xa, and the produced 3-carboxy-4-hydroxy-alinine is led into a colored substance by using a pentacyanoamineferroate method or by oxidative condensation with a suitable coupler, said colored substance being then subjected to a colorimetic determination. It is also possible to specifically determine the activity of said factor Xa by making fluorometric determinations at excitation wavelength of 328 nm and fluorescent wavelength of 540 nm.

The salient features of the present substrate, as stated above, reside in its excellent substrate specificity to said factor Xa and solubility in water. As regards the substrate specificity, the relative reactivity of the present novel substrate in various enzymes particitating in the coagulation and fibrinolysis reactions, that is, factor Xa (FXa), thrombin (TH), plasmin (PL), kallikrein (KL) and urokinase (UK) is shown in Table 1 along with those of S-2222 and S-2000N [Z-D-Lys(For)-Gly-Arg-PNA] which was synthesized by way of reference by using PNA as chromogenic group with the same aminoacid configurations as said novel substrate. In Table 1, the relative reactivity of PS-2000N (Z-D-Lys(For)-Gly-Arg-PNA) in each said enzyme is given as 100 for criterion. As seen from Table 1, the relative reactivity to thrombin, plasmin and urokinase is extremely low in the novel substrate using CHA as chromogenic group. It shows only 4% reactivity to thrombin, 1% reactivity to plasmin and 2% reactivity to urokinase. It is also noted that the novel substrate is markedly improved in selectivity in comparison with S-2222 which shows 31% reactivity to thrombin, 16% reactivity to plasmin and 40% reactivity to urokinase.

TABLE 1

| | Relative reactivity to enzymes | | | | |
|---|---|---|---|---|---|
| | Fxa | TH | PL | KL | UK |
| S-2222 | 57 | 31 | 16 | | 40 |
| Bz—Ile—Glu—Gly—Arg—PNA | (0.669) | (0.018) | (0.011) | (0.013) | (0.035) |
| PS-2000N | 100 | 100 | 100 | | 100 |
| Z—D-Lys(For)—Gly—Arg—PNA | (1.181) | (0.059) | (0.068) | (0.0) | (0.088) |
| PS-2000 | 20 | 4 | 1 | | 2 |
| Z—D-Lys(For)—Gly—Arg—CHA | (0.529) | (0.005) | (0.002) | (0.0) | (0.003) |

Initial substrate concentration $S_0 = 0.4$ mmol. Figures in the parentheses are the determined O.D. values. Determinations were made at wavelength of 405 nm ($\epsilon$ = 10,600) in S-2222 and PS-2000N and 700 nm ($\epsilon$ = 21,500) in PS-2000.

As for the solubility in water, S-2222 has a water solubility of only about 6 mmol/l while the novel substrate shows a water solubility of 20 mmol/l or above. Thus, as the novel substrate requires no specific solution aid such as a surfactant or an organic solvent, the preparation of reagents and the determination operations are very easy to control, and it is also possible to use any level of substrate concentration required for the reaction.

These facts bespeak the very excellent adaptability of the present invention as a substrate for the determination of blood coagulation factor Xa.

The primary use of the compound of the present invention is a substrate for determining the activity of blood coagulation factor Xa as already stated. In this case, the substrate is acted to the factor Xa in a buffer solution having a pH of 8.0–8.7 and the produced 3-carboxy-4-hydroxyaniline is led into a proper colored substance, this being subjected to colorimetic determinations to thereby determine the activity of the factor Xa. Fluorometric determination at an excitation wavelength of 328 nm and a fluorescent wavelength of 540 nm is also possible.

For leading said reaction product (3-carboxy-4-hydroxyaniline) into a colored substance, there can be used, for instance, a pentacyanoamineferroate method or a method in which said reaction product is subjected to oxidative condensation with a coupler. As to the coupler, an aniline compound, for example, N,N-diethylaniline can be used in case of color development on the acidic side, and phenol, naphthol, thymol, o-cresol, o-ethylphenol and the like can be used for the color development on the alkaline side.

A variety of oxidizing agents such as hydrogen peroxide, persulfate, etc., can be used as the oxidizing agent for oxidative condensation, and particularly metaperiodic acid is preferred.

By virtue of transformation of 3-carboxy-4-hydroxyaniline into a proper colored substance, the maximum wavelength distribution is confined in the range of 560-770 nm and the variation of coloration due to temperature is minimized and stabilized to provide a situation suited for the determination of factor Xa activity. A significant difference in chromogenic sensitivity is also noted. In the case of p-nitroaniline, $\epsilon=10,600$ at ordinary measuring wavelength of 405 nm, whereas in the pentacyanoamineferroate method, $\epsilon=21,500$ at $\lambda=700$ nm, and in color development by oxidative condensation, in the case of o-ethylphenol, $\epsilon=29,000$ at $\lambda=645$ nm, and in the case of 2,6-xylenol, $\epsilon=21,600$ at $\lambda=615$ nm. Such high absorbance proves to be greatly helpful for making determinations.

A prominent advantage of the present invention is that the determinations are scarcely affected by the impurities in the biotic specimen. In the case of p-nitroanilide compounds, determinations are made at a wavelength below 560 nm while according to the present invention, determinations are conducted at a wavelength above 560 nm, so that determinations are kept free of influence by the impurities in the specimen and this, coupled with the intrinsically high specificity of the substrate, makes it possible to obtain a very accurate result of determination.

From the foregoing description, it will be apparent that the compound of the present invention can provide a very excellent substrate to be used for determining the activity of blood coagulation factor Xa as compared with the conventional ones.

The compound of the present invention represented by the general formula (I) can be synthesized by a method well known in peptide chemistry.

As α-amino protective group, it is advantageous to use carbobenzoxy or t-butyloxycarbonyl or the groups associated therewith such as p-methoxycarbobenzoxy, p-nitrocarbobenzoxy or p-methoxyphenylazolecarbobenzoxy.

Protection of δ-guanidyl group of arginine can be advantageously accomplished by protonization means. Coupling of two amino acids or coupling of dipeptide and amino acid can be effected by the activation of α-carboxyl group. For such coupling, N-hydroxysuccinic imide, p-nitrophenol, trichlorophenol, 4,6-dimethylpyrimidyl-2-thiol and the like can be used. Said activation into an ester derivative is advantageously conducted in the presence of a carbodiimide such as N,N-dicyclohexylcarbodiimide (DCC).

For the synthesis of the substrate, a method is used in which chromogenic group is first bonded to arginyl group, followed by successive coupling. Alternatively, N-terminated dipeptide fragment itself may be first synthesized and it is then bonded to arginyl group having chromophoric group.

The present invention will be described in further detail below by way of the embodiments thereof, but it is to be understood that the present invention is not limited only to the scope of these embodiments.

Notice is to be taken of the following matters in reading through the Examples given below.

(1) Abbreviations

Lys=lysine
Gly=glycine
Arg=arginine
Sar=sarcosine
Orn=ornithine
Z=benzyloxycarbonyl
BOC=t-butyloxycarbonyl
Ac=acetyl
For=formyl
DMF=dimethylformamide
MeOH=methanol
NEM=N-ethylmorpholine
-PNA=p-nitroanilide
-CHA=3-carboxy-4-hydroxyanilide
TLC=thin layer chromatography
GPC=gel permeation chromatography
AcOH=acetic acid
BuOH=n-butanol
AcOEt=ethyl acetate
Osu=succinimide (Note: Amino acids are all L-type unless otherwise noted.)

(2) Thin layer chromatography (TLC)

Silica gel $F_{254}$ plate (manufactured by E. Merck A.G.) was used for TLC analysis.
Solvents used:
Rf$_1$ n-BuOH:AcOH:H$_2$O=4:1:1
Rf$_2$ n-BuOH:AcOH:H$_2$O=4:1:2
Rf$_3$ n-BuOH:AcOH:H$_2$O=4:1:5

(3) Gel filtration

Polyvinyl gel "TOYOPEARL HW40F" (manufactured by Toyo Soda Mfg. Co., Ltd.) was used for gel filtration.

EXAMPLE 1

Synthesis of Z-D-Lys(For)-Gly-Arg-CHA

I. BOC-Arg-CHA.HCl 381.1 Grams (1.16 mol) of BOC-Arg-OH.HCl.H$_2$O was dissolved in 1,392 ml of DMF, and then 151 ml of NEM was added thereto, followed by dropwise addition of 152.3 ml of isobutyl chloroformate at $-20°$ C. After 10 minutes reaction, a 928 ml DMF solution of 219.8 g (1.16 mol) of 5-aminosalicylic acid hydrochloride and 301.6 ml of NEM was added dropwise to said reaction mixture at $-15°$ to $-10°$ C. The reaction was continued for 3 hours at the same temperature and additionally continued for 15 hours at room temperature. After the reaction was completed, the DMF was removed by evaporation under a reduced pressure and the residue obtained was dissolved in 464 ml of MeOH and 332 ml of n-BuOH. To the mixture was added with 3,300 ml of AcOH, washed twice with 2,160 ml of cold 5% hydrochloric acid saturated with sodium chloride, then dried with anhydrous magnesium sulfate. After drying, the magnesium sulfate was removed by filtration and the solvent was removed by evaporation under a reduced pressure to obtain 464.8 g (89.9%) of BOC-Arg-CHA.HCl. Rf$_1$=0.64. Melting point: 225.0° C. (decomposed). $[\alpha]_D^{20}-10.7$ (C=1, MeOH).

| Elementary analysis (for $C_{26}H_{50}N_5O_9Cl$) | | | |
| --- | --- | --- | --- |
| | C | H | N |
| Calculated (%): | 51.01 | 8.23 | 11.44 |
| Found (%): | 50.79 | 8.04 | 11.52 |

II. BOC-Gly-Arg-CHA.HCl 243.7 Grams (0.55 mol) of BOC-Arg-CHA.HCl was dissolved in 1,093 ml of 2N-HCl/AcOH and a small quantity of MeOH, and the mixture was reacted at room temperature for 1 hour. After the reaction was completed, to the reaction mixture was added with 1,093 ml of isopropanol and reprecipitated in AcOEt. The crystals precipitated were collected by filtration and dried to obtain 156.2 g (74.3%) of H-Arg-CHA.2HCl. $Rf_3=0.15$. Melting point: 240.5° C. (decomposed). $[\alpha]_D^{20}+53.5$ (C=1, H$_2$O)

109.2 Grams (0.27 mol) of H-Arg-CHA.2HCl was dissolved in 290 ml of DMF and then 70.2 ml (0.54 mol) of NEM was added thereto, followed by further addition of 81.7 g (0.3 mol) of BOC-Gly-OSu at 0° to 5° C. and the reaction was carried out at room temperature for 18 hours. After the reaction was completed, the DMF was removed by evaporation under a reduced pressure and the residue was dissolved in 500 ml of MeOH and reprecipitated in 8 liters of AcOEt. The crystals precipitated were collected by filtration and dried to obtain 135.8 g (100%) of BOC-Gly-Arg-CHA.HCl. $Rf_1=0.46$. Melting point: 214.5° C. (decomposed). $[\alpha]_D^{20}-22$ (C=1, MeOH)

| Elementary analysis (for $C_{20}H_{30}N_6O_7.HCl.H_2O$) | | | |
|---|---|---|---|
| | C | H | N |
| Calculated (%): | 46.11 | 6.39 | 16.13 |
| Found (%): | 46.55 | 6.80 | 16.15 |

III. Z-D-Lys(For)-Gly-Arg-CHA.HCl 125.7 Grams (0.25 mol) of BOC-Gly-Arg-CHA.HCl was dissolved in a small quantity of MeOH and to the solution was added with 500 ml of 2N-HCl/AcOH and the mixture was reacted under stirring at room temperature for 1 hour. After the reaction was completed, the reaction mixture was reprecipitated in 4.5 liters of diethyl ether and the crystals precipitated were collected by filtration and dried to obtain 109.8 g (100%) of H-Gly-Arg-CHA.2HCl. $Rf_3=0.09$. Melting point: 219.5° C. (decomposed). $[\alpha]_D^{20}-21.0$ (C=1, AcOH:-H$_2$O=1:1).

4.4 Grams (10 mM) of H-Gly-Arg-CHA.2HCl was dissolved in 20 ml of 0.75N-NEM/DMF and to the mixture was added with 8.1 g (20 mM) of Z-D-Lys(-For)-OSU under stirring and cooling at 0°-5° C. and the reaction was carried out at room temperature for 15 hours. After the reaction was completed, the solvent was remofed by evaporation under a reduced pressure and the residue obtained was dissolved in methanol and reprecipitated in 800 ml of AcOEt. The crystals precipitated were collected by filtration and dried to obtain crude Z-D-Lys(For)-Gly-Arg-CHA.HCl. This crude product was purified by means of a column chromatography by using "TOYOPEARL HW 40F" column and by using MeOH as a developing solvent to obtain 3.6 g (52.2%) of Z-D-Lys(For)-Gly-Arg-CHA.HCl. $Rf_1=0.40$. Melting point: Hydroscopic $[\alpha]_D^{20}-13.6$ (C=0.5, AcOH:H$_2$O=1:1)

| Elementary analysis (for $C_{30}H_{40}N_8O_9.HCl.2.5H_2O$) | | | |
|---|---|---|---|
| | C | H | N |
| Calculated (%): | 48.74 | 6.28 | 15.18 |

-continued

| Elementary analysis (for $C_{30}H_{40}N_8O_9.HCl.2.5H_2O$) | | | |
|---|---|---|---|
| | C | H | N |
| Found (%): | 48.50 | 6.18 | 15.60 |

EXAMPLE 2

Synthesis of Z-D-Lys-Gly-Arg-CHA

I. Z-D-Lys(BOC)-Gly-Arg-CHA.HCl 8.8 Grams (20 mM) of H-Gly-Arg-CHA.2HCl was dissolved in 21.5 ml of DMF, to this solution was added 5.1 ml (40 mM) of NEM. To the mixture was further added with 9.6 g (20 mM) of Z-D-Lys(BOC)-OSu and reacted at room temperature for 18 hours. After the reaction was completed, the DMF was removed by evaporation under a reduced pressure and the residue obtained was dissolved in MeOH and reprecipitated in 1 liter of AcOEt. The crystals precipitated were collected by filtration and dried to obtain 14.9 g (97.4%) of Z-D-Lys(BOC)-Gly-Arg-CHA.HCl. $Rf_1=0.50$. Melting point: 207.5° C. (decomposed). $[\alpha]_D^{20}-8.0$ (C=0.5, MeOH)

| Elementary analysis (for $C_{34}H_{48}N_8O_{10}.HCl.1.5H_2O$) | | | |
|---|---|---|---|
| | C | H | N |
| Calculated (%): | 51.54 | 6.62 | 14.14 |
| Found (%): | 51.64 | 6.81 | 13.61 |

II. Z-D-Lys-Gly-Arg-CHA.2HCl 2.7 Grams (3.5 mM) of Z-D-Lys(BOC)-Gly-Arg-CHA.HCl was dissolved in a small amount of MeOH, followed by addition of 7 ml of 2N-HCl/AcOH and the mixture was reacted at room temperature for 1 hour. The reaction mixture was reprecipitated from dry diethyl ether and the crystals precipitated were collected by filtration and dried to obtain crude Z-D-Lys-Gly-Arg-CHA.2HCl. This crude product was purified by means of a column chromatography by using "TOYO-PEARL HW 40F" column using MeOH as a developing solvent to obtain 1.8 g (74.6%) of Z-D-Lys-Gly-Arg-CHA.2HCl. $Rf_2=0.31$. Melting point: 220.0° C. (decomposed). $[\alpha]_D^{20}-16.0$ (C=1, 50% AcOH).

| Elementary analysis (for $C_{29}H_{40}O_8N_8.2HCl.2.2H_2O$) | | | |
|---|---|---|---|
| | C | H | N |
| Calculated (%): | 46.99 | 6.28 | 15.12 |
| Found (%): | 47.08 | 5.89 | 14.94 |

EXAMPLE 3

By a method similar to that described in the above-mentioned Examples, there were prepared substrates as follows:

PS-2003: Z-D-Lys-(Ac)-Gly-Arg-CHA.HCl
  Melting point: 219.5° C. (decomposed)
  $Rf_1=0.45$ $[\alpha]_D^{20}-12.0$ (C=0.5, 50% AcOH)

| Elementary analysis | | | |
|---|---|---|---|
| | C | H | N |
| Calculated (%): | 50.10 | 6.37 | 15.08 |

-continued

| Elementary analysis | | | |
|---|---|---|---|
| | C | H | N |
| Found (%): | 50.34 | 6.12 | 14.85 |

PS-2004: Z-D-Orn(Ac)-Gly-Arg-CHA.HCl
Melting point: 130–146
$Rf_1 = 0.37$
$[\alpha]_D^{20} -9.2$ (C=0.5, 50% AcOH)

| Elementary analysis | | | |
|---|---|---|---|
| | C | H | N |
| Calculated (%): | 48.74 | 6.28 | 15.18 |
| Found (%): | 48.74 | 6.20 | 15.56 |

PS-2005: Z-D-Lys-Sar-Arg-CHA.2HCl
Melting point: 215.0° C. (decomposed)
$Rf_3 = 0.34$
$[\alpha]_D^{20} -25.0$ (C=0.5, 50% AcOH)

| Elementary analysis | | | |
|---|---|---|---|
| | C | H | N |
| Calculated (%): | 47.37 | 6.49 | 14.73 |
| Found (%): | 47.47 | 6.13 | 14.85 |

PS-2006:

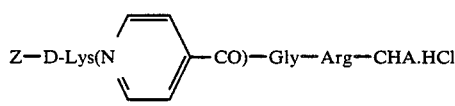

Z—D-Lys(N⌬—CO)—Gly—Arg—CHA.HCl

Melting point: 144.5°–157.0° C.
$Rf_1 = 0.39$
$[\alpha]_D^{20} -4.9$ (C=0.5, 50% AcOH)

| Elementary analysis | | | |
|---|---|---|---|
| | C | H | N |
| Calculated (%): | 50.04 | 5.66 | 14.59 |
| Found (%): | 49.88 | 5.86 | 14.96 |

EXAMPLE 4

The specificities of newly synthesized substrates were tested by reacting them with various enzymes as follows.

(1) Substrate solution: 2 mM/liter of $H_2O$
(2) Buffer solutions: The concentrations of each of tris(-hydroxymethyl)aminomethane [hereinafter referred to as "Tris"], NaCl and $CaCl_2$, as well as pH were specified as follows for the respective enzymes.

| Buffer solution | $FX_a$ | Thrombin | Plasmin | Kallikrein | Urokinase |
|---|---|---|---|---|---|
| Tris (mM) | 50 | 50 | 50 | 50 | 50 |
| NaCl (mM) | 500 | 150 | 150 | 150 | 150 |
| $CaCl_2$ (mM) | 5 | 0 | 0 | 0 | 0 |
| pH (at 25° C.) | 8.5 | 8.5 | 7.8 | 7.8 | 8.2 |

(3) Enzymes used:

| Enzyme | Origin | Manufacturer | Lot No. | Unit |
|---|---|---|---|---|
| $FX_a$ | Human | Bohringer Mannheim, GmbH, West Germany | 1,352,304 | 0.5 U/ml |
| Thrombin | Bovine | Mochida Pharmaceutical Co., Ltd., Japan | 65,146 | 1.0 NIH/ml |
| Plasmin | Human | The Green Cross Corporation, Japan | PL-35 | 0.25 CU/ml |
| Kallikrein | Swine | Sigma Chemical Co., U.S.A. | 32 F-0810 | 1.0 U/ml |
| Urokinase | Human | Mochida Pharmaceutical Co., Ltd., Japan | 2C 239 | 1,000 U/ml |

(4) Reaction Stopper (PNA): 10%-acetic acid
(5) Color forming agent (CHA): Pentacyanoaminoferroate
(6) Method of determination:

0.3 Milliter buffer solution and 0.1 ml of enzyme reagent were collected in a hard glass test tube of which surface being treated with silicone, or a plastic test tube and preheated in a thermostat at 37° C. for 5 minutes. Precisely 5 minutes after the reaction was started, 2.0 ml of reaction stopper solution or reactionterminating color forming reagent was added to terminate the enzyme reaction. The reaction mixture was allowed to stand at 37° C. for 10 minutes and then the adsorbance at 405 nm or 700 nm was measured.

The results are shown in Table 2 below.

TABLE 2

| | Substrate | | FXa | TH | PL | KL | UK |
|---|---|---|---|---|---|---|---|
| 1. | S-2222 | Bz—Ile—Glu(OR)—Gly—Arg—PNA | 0.669 | 0.018 | 0.011 | 0.013 | 0.035 |
| 2. | S-2337 | Ba—Ile—Glu(N⌬)—Gly—Arg—PNA | 0.576 | 0.025 | 0.008 | 0.0 | 0.024 |
| 3. | PS-2000N | Z—D-Lys(For)—Gly—Arg—PNA | 1.181 | 0.059 | 0.068 | 0.0 | 0.088 |
| 4. | PS-2000 | Z—D-Lys(For)—Gly—Arg—CHA | 0.529 | 0.005 | 0.002 | 0.0 | 0.003 |
| 5. | PS-2001 | Z—D-Lys—Gly—Arg—CHA | 0.314 | 0.006 | 0.005 | 0.0 | 0.004 |
| 6. | PS-2002 | Z—D-Lys(Ac)—Gly—Arg—CHA | 0.426 | 0.009 | 0.004 | 0.0 | 0.003 |
| 7. | PS-2003 | Z—D-Orn(Ac)—Gly—Arg—CHA | 0.344 | 0.004 | 0.0 | 0.0 | 0.0 |
| 8. | PS-2004 | Z—D-Lys—Sar—Arg—CHA | 0.292 | 0.006 | 0.0 | 0.0 | 0.0 |

TABLE 2-continued

| Substrate | | FXa | TH | PL | KL | UK |
|---|---|---|---|---|---|---|
| 9. PS-2005 | Z—D-Lys(N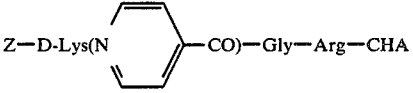CO)—Gly—Arg—CHA | 0.289 | 0.007 | 0.003 | 0.0 | 0.004 |

[Initial substrate concentration $S_o$ = 0.4 mM/l. Figures are the measured values of absorbance (O.D.). Measurements were conducted at wavelength of 405 nm for the substrate Nos. 1–3, and at wavelength of 700 nm for the substrate Nos. 4–9.]

What is claimed is:

1. A novel substrate for determining the activity of blood coagulation factor Xa (Stuart-Prower factor), said substrate having the property of developing color or becoming fluorescent when combined with said factor Xa or factor Xa-like enzymes, said substrate being composed of a compound represented by the general formula:

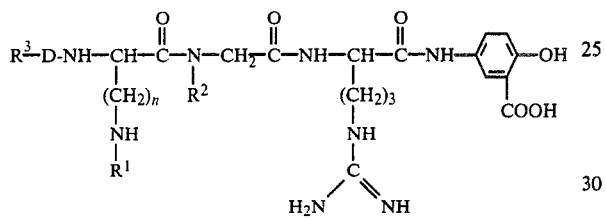

[wherein n is an integer of 3–4; $R^1$ is a hydrogen atom or a group of the formula

$R^2$ is a hydrogen atom, a methyl group or a phenyl group; $R^3$ is a group of the formula

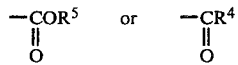

(wherein $R^4$ is a hydrogen atom, a methyl group, a phenyl group or a group of the formula

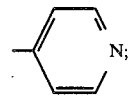

and $R^5$ is a group of the formula

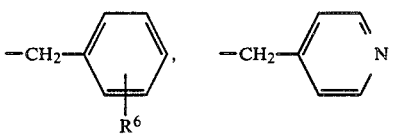

or —C(CH$_3$)$_3$, wherein $R^6$ is a hydrogen atom or a methoxy group)], characterized in that said compound contains 3-carboxy-4-hydroxyanilide (CHA) group in its molecule as the chromogenic group.

* * * * *

UNITED STATES PATENT AND TRADEMARK OFFICE
CERTIFICATE OF CORRECTION

PATENT NO. : 4,622,389

DATED : November 11, 1986

INVENTOR(S) : Nagasawa et al

It is certified that error appears in the above-identified patent and that said Letters Patent is hereby corrected as shown below:

On the cover page, column 1, cancel "NITTO POSEKI CO., LTD." . Substitute --Nitto Boseki Co., Ltd.--

Signed and Sealed this

Third Day of February, 1987

Attest:

DONALD J. QUIGG

Attesting Officer

Commissioner of Patents and Trademarks